United States Patent [19]

DeHart

[11] Patent Number: 4,819,630

[45] Date of Patent: Apr. 11, 1989

[54] FLEXIBLE LIGHT TRANSMISSIVE APPARATUS AND METHOD

[75] Inventor: Anthony G. DeHart, Winter Park, Fla.

[73] Assignee: Laser Photonics, Inc., Orlando, Fla.

[21] Appl. No.: 28,388

[22] Filed: Mar. 20, 1987

[51] Int. Cl.$^4$ ............................................. A61B 17/36
[52] U.S. Cl. ................................. 128/303.1; 128/398; 350/96.29
[58] Field of Search ......................... 128/4–8, 128/303.1, 395–398, 634; 362/32; 350/96.22, 96.26, 96.29; 604/21, 96

[56] References Cited

U.S. PATENT DOCUMENTS

| | | | |
|---|---|---|---|
| 3,821,510 | 6/1974 | Muncheryan | 128/395 |
| 3,843,865 | 10/1974 | Nath | 128/395 |
| 4,129,356 | 12/1978 | Oestreich | 350/96.29 |
| 4,306,546 | 12/1981 | Heine et al. | 128/6 |
| 4,375,314 | 3/1983 | Sakuragi et al. | 350/96.29 |
| 4,418,688 | 12/1983 | Loeb | 128/6 |
| 4,458,683 | 7/1984 | Saito et al. | 128/395 |
| 4,564,011 | 1/1986 | Goldman | 128/303.1 |
| 4,569,335 | 2/1986 | Tsuno | 128/6 |
| 4,592,353 | 6/1986 | Daikuzno | 128/303.1 |

FOREIGN PATENT DOCUMENTS

| | | | |
|---|---|---|---|
| 0112527 | 7/1984 | European Pat. Off. | 128/6 |
| 2820239 | 11/1978 | Fed. Rep. of Germany | 128/6 |

Primary Examiner—Max Hindenburg
Attorney, Agent, or Firm—Duckworth, Allen, Dyer & Doppelt

[57] ABSTRACT

An optical energy transmission device and a related method includes a flexible fiber optic rod and a flexible sheath surrounding and spaced from the fiber optic rod, with a disc member fixed in edge contact with both the rod and the sheath for supporting and uniformly spacing the rod from the sheath. The inner and outer periphery of the disc is arched in order to permit cooling fluids to pass relatively unimpeded along the passageway along the rod and the outer sheath, while maintaining the desired position of the rod relative to the sheath.

14 Claims, 3 Drawing Sheets

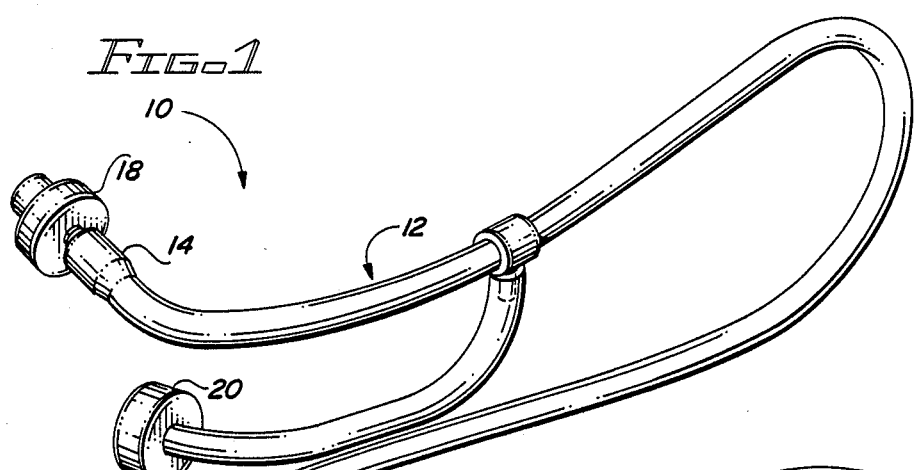
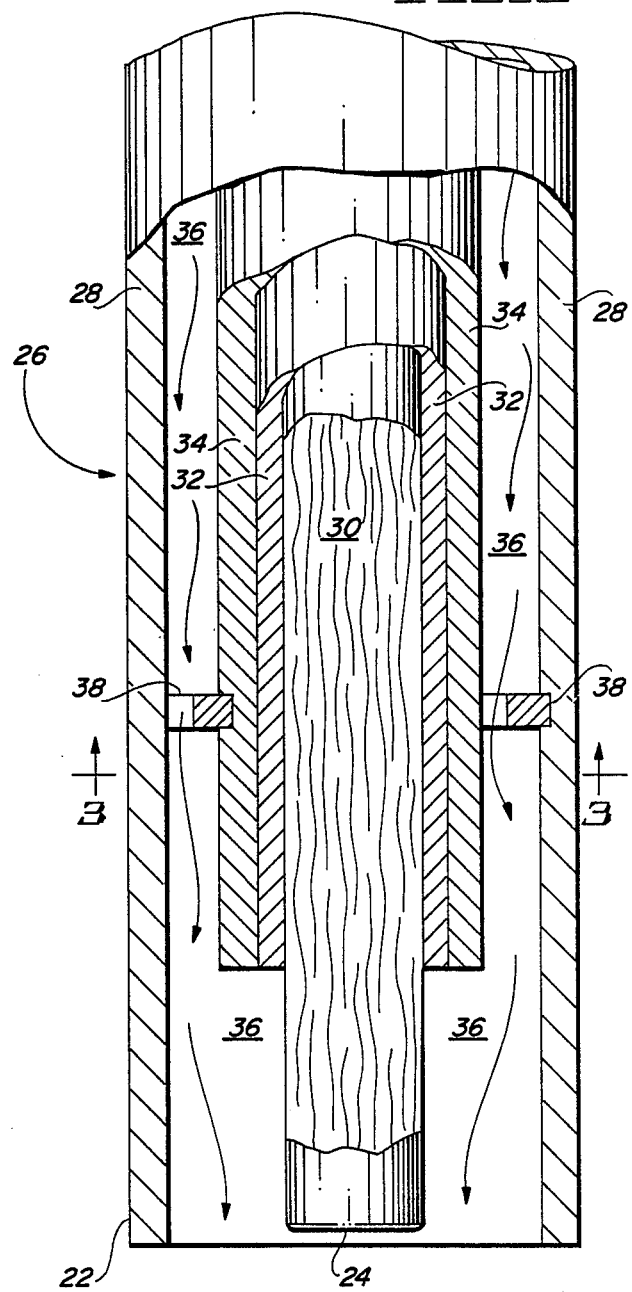
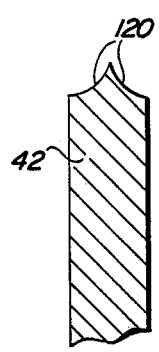
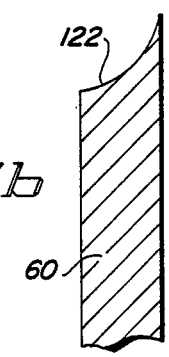
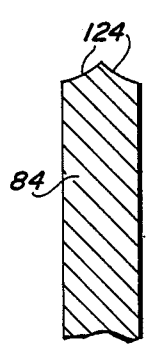

FLEXIBLE LIGHT TRANSMISSIVE APPARATUS AND METHOD

BACKGROUND OF THE INVENTION

1. Field of the Invention

The present invention relates to light transmissive optical devices and method, and has particular utility in the medical devices field as a laser catheter which can be percutaneously inserted into a cavity in the human body such as the esophogus, lungs and digestive system.

2. Description of the Prior Art

The prior art teaches a number of flexible, optically transmissive catheter arrangements for insertion into the human body. See for example the following U.S. Pat. Nos.: 4,175,545 to Termanini; 3,821,510 to Muncheryan; 3,866,599 to Johnson; 4,445,892 to Hussein et al.; 4,207,874 to Choy; 4,418,688 to Loeb; and 4,592,353 to Daikuzono.

Nonpatent literature references discussing the use of flexible laser catheters is also set forth in the following articles: "Laser Coronary Angioplasty: Experience with 9 Cadaver Hearts" by Daniel S. J. Choy, et al, *The American Journal of Cardiology*, Vol. 50, December 1982; "Transluminal Laser Catheter Angioplasty" by Daniel S. J. Choy, et al, *The American Journal of Cardiology*, Vol. 50, December 1982; "Effects of Carbon Dioxide, Nd-YAG," and Argon Laser Radiation on Coronary Atheromotous Plaques by George S. Abela, et al, *The American Journal of Cardiology*, Vol. 50, December 1982; "Laser Irradiation of Human Atherosclerotic Obstructive Disease: Simultaneous Visualization and Vaporization Achieved by a dual Fiberoptic Catheter" by Garrett Lee, et al, *American Heart Journal*, January, 1983; "Effects of Laser Irradiation on Human Thrombus: Demonstration of a Linear Disssolution-Dose Relation Between Clot Length and Energy Density" by Garrett Lee, et al, *The American Journal of Cardiology*, Vol. 52, October 1983; "Vaporization of Human Thrombus by Laser Treatment" by Garrett Lee, et al, *American Heart Journal*, August 1982; "Possible Laser Vaporization of Arterial Wall Lesions Set", *Cardiology Times*, October 1983; "Arterial Response to Laser Operation for Removal of Artherosclerotice Plaques" by Ross G. Gerrity, et al, *The Journal, Thoracic and Cardiovascular Surgery*, Vol. 85, No. 3, March 1983; and "Laser Angioplasty: Effects on Coronary Artery Stenosis" by H. Geschwind, et al, *The Lancet*, Nov. 12, 1983.

There have been commercially available fiber optic rod catheters employing a distal nozzle fixture for holding the distal end of the fiber optic rod at the extremity of the catheter. Such a device has been manufactured by Molectron Corporation of Sunnyvale, California and consists of an elongated metal spacer into which the fiber optic rod extends and which is threaded inside the sheath. The spacer includes longitudinal flutes along the outside of the spacer for permitting cooling fluids to pass. Another such commercial device has been manufactured by Cooper Lasersonics and MBB (a German medical device manufacturing consortium). As understood, that arrangement is also an elongated metal spacer into which the fiber optic rod is threaded, with longitudinal flutes permitting passage of a cooling fluid, and with an outside hose barb permitting interconnection with the outermost catheter sheath.

SUMMARY OF THE INVENTION

The present invention contemplates an optical energy transmission device and method including a fiber optic rod with a sheath surrounding and spaced from the fiber optic rod and having means for fixing the rod within the sheath with uniform spacing between the rod and the sheath along the length thereof. The fixing means comprises a disc spaced along the length of the rod, each disc member including a central opening for receiving the fiber optic rod, and including three or more inwardly-facing portions extending from the inner periphery of the central opening and into supporting contact with the fiber optic rod. Suitably, the fiber optic rod includes an outer sleeve along the periphery thereof with the inwardly-facing supporting portions extending into the sleeve in order to fix the disc with the rod. The periphery of the opening defined by the inwardly-facing portions form plural arches, each arch forming a void between its inner extremity and the outer periphery of the sleeve whereby plural passageways through each disc member is provided along the outer periphery of the fiber optic rod so that cooling fluids may pass in a relatively uninterrupted manner.

Further in accordance with the preferred embodiment, each disc member includes three or more outwardly-facing portions along the outer periphery thereof, each outwardly-facing portion extending into edge contact with the inner periphery of the outermost sheath to likewise fix each disc member relatively immovable with respect to the sheath. The outer periphery of each disc forms plural arches between adjacent outwardly-facing portions, so that each outer arch forms a void between its inner extremity and the inner periphery of the sheath, whereby passage of cooling fluids is further enhanced.

While the inner and outer periphery of the disc members may be provided with as few as three inwardly-facing and three outwardly-facing portions in order to achieve rigidity in uniform spacing, it has been found preferable because of the relative dimensions involved to provide at least four inwardly-facing portions and at least four outwardly-facing portions, in order to achieve a high degree of relative strength along each inner and outer arch, while maintaining a high degree of rigidity.

In one embodiment, the inwardly and outwardly facing portions are formed of tip ends having a reduced dimension to lock with an outer sleeve surrounding the fiber optic rod through edge contact.

In order to assist in placing the disc member in the desired location, the disc preferably has a discontinuity about its periphery extending to the central opening. The sides of the disc adjacent the discontinuity are expanded to permit the disc to fit over the rod and sleeve at its distal end, and to thereafter draw back into contact with the sleeve.

DESCRIPTION OF THE DRAWINGS

FIG. 1 is a perspective view, partially broken away, of an optically transmissive catheter in accordance with the present invention.

FIG. 2 is an enlarged, cross-sectional view of a portion of the catheter shown in FIG. 1 taken along the lines 2—2'.

FIGS. 7A, B and C show various tip end constructions for the various disc members shown in FIGS. 3–6.

DETAILED DESCRIPTION OF THE PREFERRED EMBODIMENT

Figure 3:
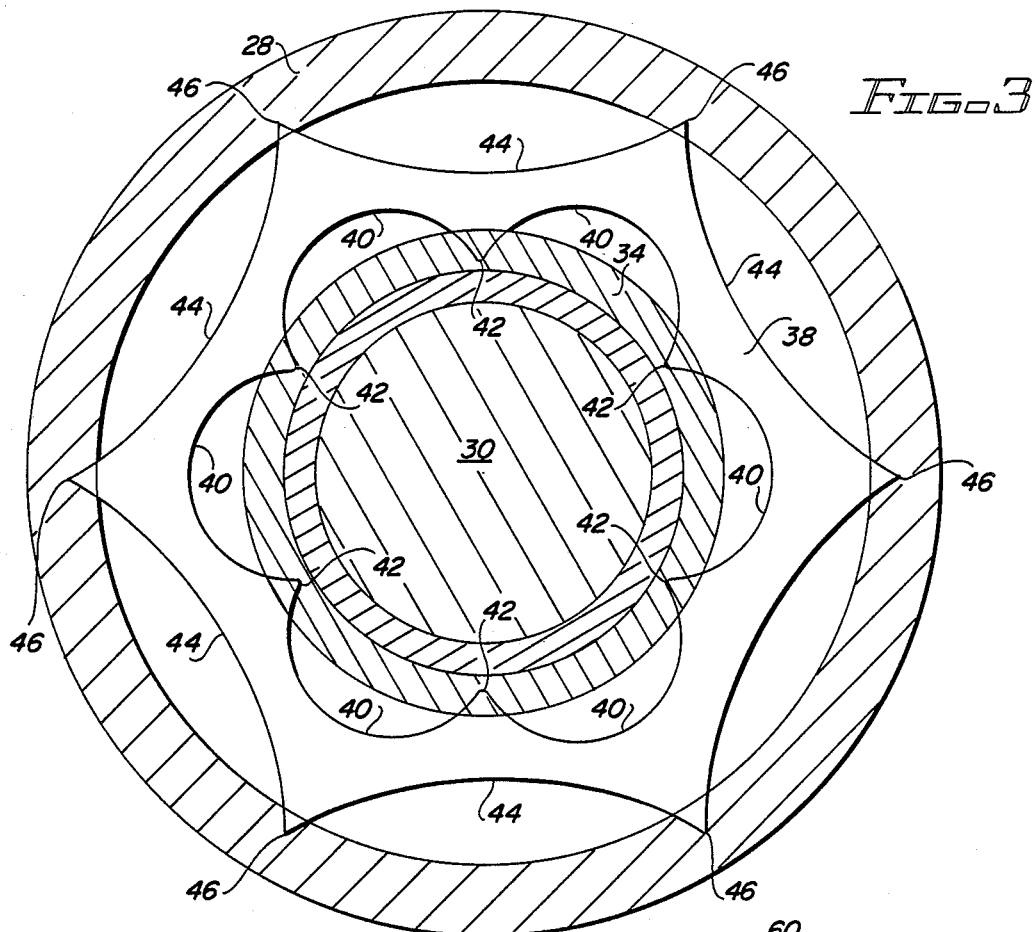
FIG. 3 is a cross-sectional front elevation of the construction shown in FIG. 2, taken along the lines 3—3'.

A first embodiment of the present invention will now be described as a flexible laser catheter useful for percutaneous insertion into a body cavity.

The catheter 10 includes a flexible body member 12 having a proximal end 14 at which there is a conventional optical feed coupling 18 and a conventional coupling 20 for injecting cooling fluids along the flexible catheter 10. The catheter 10 further includes a distal end 22 having an optical probe end 24 through which light transmitted from the coupler 18, along the catheter body 12 to the distal end 22 is emitted for medical treatment purposes. The flexible body 12 includes a portion 26 which is shown in cross-section in FIG. 2 and described next.

The flexible catheter body 12 is, of course, essentially identical along its length between the proximal and distal ends 14 and 22 as the portion 26 shown in FIG. 2.

The portion 26 includes an outer, flexible sheath 28 having a hollow longitudinal core 29 with a fiber optic rod 30 extending axially through the sheath. The fiber optic rod 30 includes an outer sleeve defined in this specific example by an inner silicone cladding 32 and an outer teflon buffer 34. The hollow longitudinal core 29 of the sheath 28 has a substantially greater inner diameter than the diameter of the outer periphery of the combination of the rod 30 and sleeve 32, 34 so as to define a void 36, and so as to permit a cooling fluid (shown by arrows in FIG. 2) to pass along the outer periphery of the rod-sleeve combination.

In accordance with the present invention, means are provided for supporting the fiber optic rod 30 and its associated sleeve 32, 34 within the sheath 28 for uniformly spacing the rod from the sheath adjacent the distal end 24 and for fixing the rod 30 relative to the sheath. To this end there is provided a spacing member at the distal end 14, in the form of a disc-shaped member having a central opening for receiving the combination of the fiber optic rod 30 and the sleeve 32, 34.

One embodiment of the disc member 38 is now described with reference to FIG. 3. As shown, the central opening of each disc member 38 is defined, in the specific embodiment of FIG. 3, by six inwardly-facing tip ends extending into edge contact with the sleeve 32, 34 and preferably partially through the outer buffer 34 (note FIG. 3). Between adjacent tip ends 42, the inner periphery of the opening of the disc member 38 is defined by a generally semi-circular arch 40 which forms a void between the inner extremity of each arch 40 and the outer periphery of the silicone layer 34. Each void permits the passage of cooling fluids injected along the void 36 via the coupling 20.

Likewise the outer periphery of the disc member 38 is provided, in the embodiment of FIG. 3, with six outwardly-facing tip ends 46 and with generally circular arches 44 defined between adjacent tip ends. Each arch 44 defines a passageway for cooling fluids between its innermost extremity and the inner periphery of the sheath 28. In a manner similar to the inwardly-facing tip ends 42, the outwardly-facing tip ends 46 extend partially into the sheath 28. Thus, the disc member 38 rigidly fixes the fiber optic rod 30 in a relatively uniform position with respect to the inner periphery of the sheath 28 at the distal end 14. While it might be feasible to use as few as three tip ends both on the inner and outer periphery of the disc member 38, it has been found preferable to utilize at least six tip ends in the construction of FIG. 3, in order to achieve a relative degree of uniform spacing around the fiber optic rod.

Figure 4:
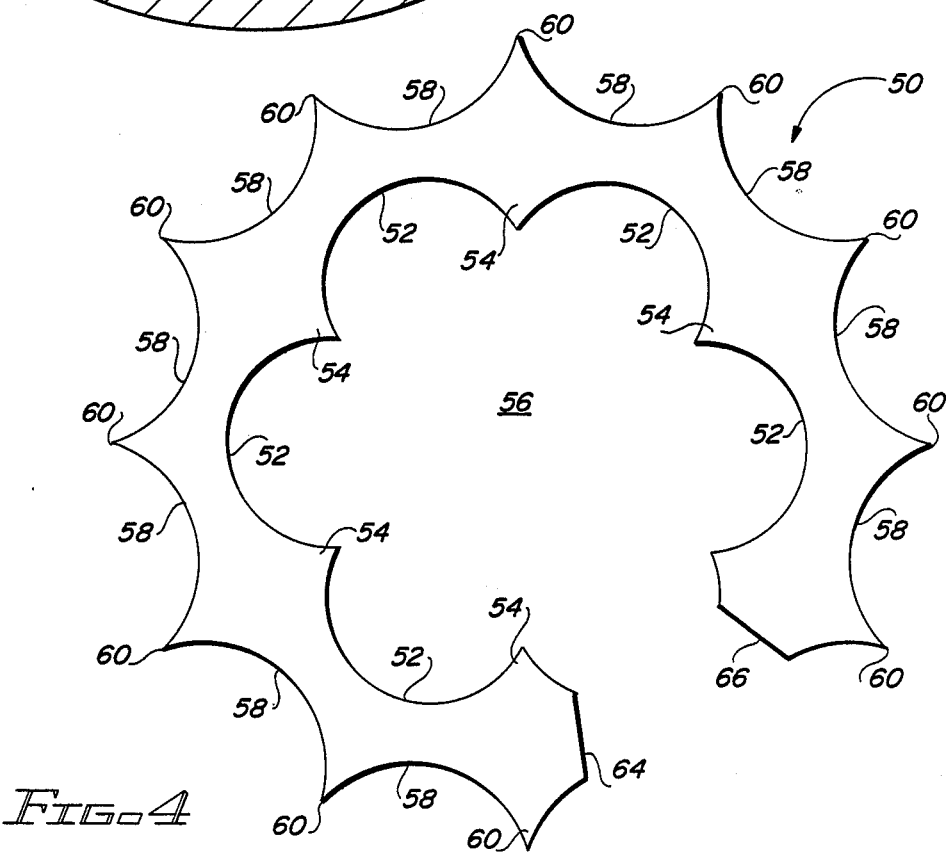
FIG. 4 is a front elevation of another embodiment of a disc member serving a function similar to the disc member 38 in FIG. 3.

In an alternate arrangement shown in FIG. 4, a disc member 50 is provided with inner arches 52 and inwardly-facing tip ends 54 defining a central opening 56 which is intended to support and uniformly space the fiber optic rod 30 in the manner described above with reference to FIG. 1–3. The disc member 50 further includes outer arches 58 and outwardly-facing tip ends 60 serving a function similar to the arches 44 and tip ends 46 in FIG. 3. Further, the disc member 50 in FIG. 4 is provided with a discontinuity 62 along the body portion thereof, which discontinuity 62 is defined by surfaces 64 and 66. This discontinuity may be utilized with an appropriate tool to press the discontinuity surfaces 64 and 66 apart, thus permitting the disc to be extended over the sleeve 34 for positioning. Thereafter, the disc may be released causing the inwardly-facing tip ends 54 to engage and extend into the sleeve 34, and further permit the sheath 28 to be passed over the outwardly-facing tip ends 60. The sheath 28 is then crimped to lock the tip ends 60 into the sheath at the distal end 14.

Figure 5:
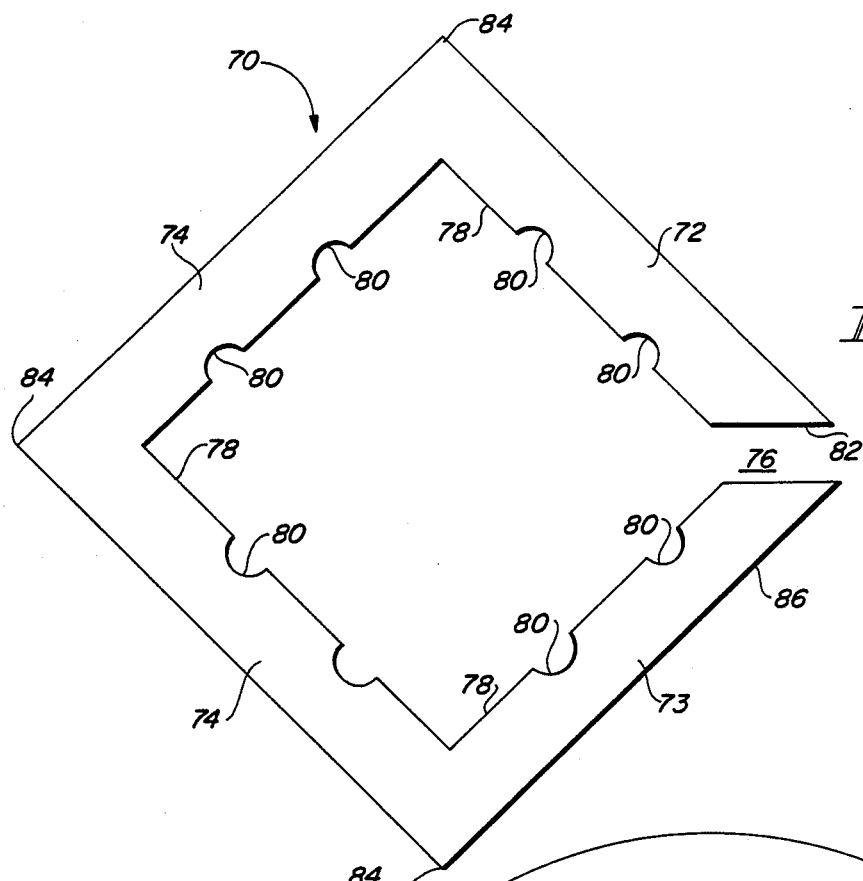
FIG. 5 is a front elevation of another embodiment of a disc member serving a function similar to the disc member 38 in FIG. 3.

In the embodiment of FIG. 5, the disc member 70 has a generally rectangular configuration having four arms 72–75 and defining a central opening engaged about the sleeve 76 of the fiber optic rod (not shown). The disc member 70 includes arches 78 like the arches 40 and 52 of FIGS. 3 and 4 for passage of the cooling fluid. The inner periphery of each arm 72–75 engages the outer sleeve 76 of the fiber optic rod (not separately shown) and is locked and fixed with respect to the sleeve 76 via small scooped openings 80 along each arm. The peripheral edges of each arm 72–75 may also be provided with a sharpened surface like that shown and described below with reference to FIGS. 7A–7C to further ensure that the disc member 70 is locked and fixed with respect to the sleeve 76.

The disc member 70 further includes outwardly-facing tip ends 83 engaging the sheath 86 to hold the entire combination of the fiber optic rod and sleeve 76 in place. The disc member 70 further includes a discontinuity 82 to facilitate the expansion of the central opening defined by the inner periphery of the arms 72–75 so as to fit over the sleeve 76, and thereafter permitting the disc member 70 to lock in place along the outer periphery of the sleeve 76. The outer sheath 86 is then expanded at the distal end 14 and slipped over the disc 70. The sheath 86 is then crimped in the area adjacent the distal end of the associated catheter (as distal end 14 in FIG. 1) to obtain a locking of the outwardly-facing tip ends 84 into the sheath 86.

Figure 6:
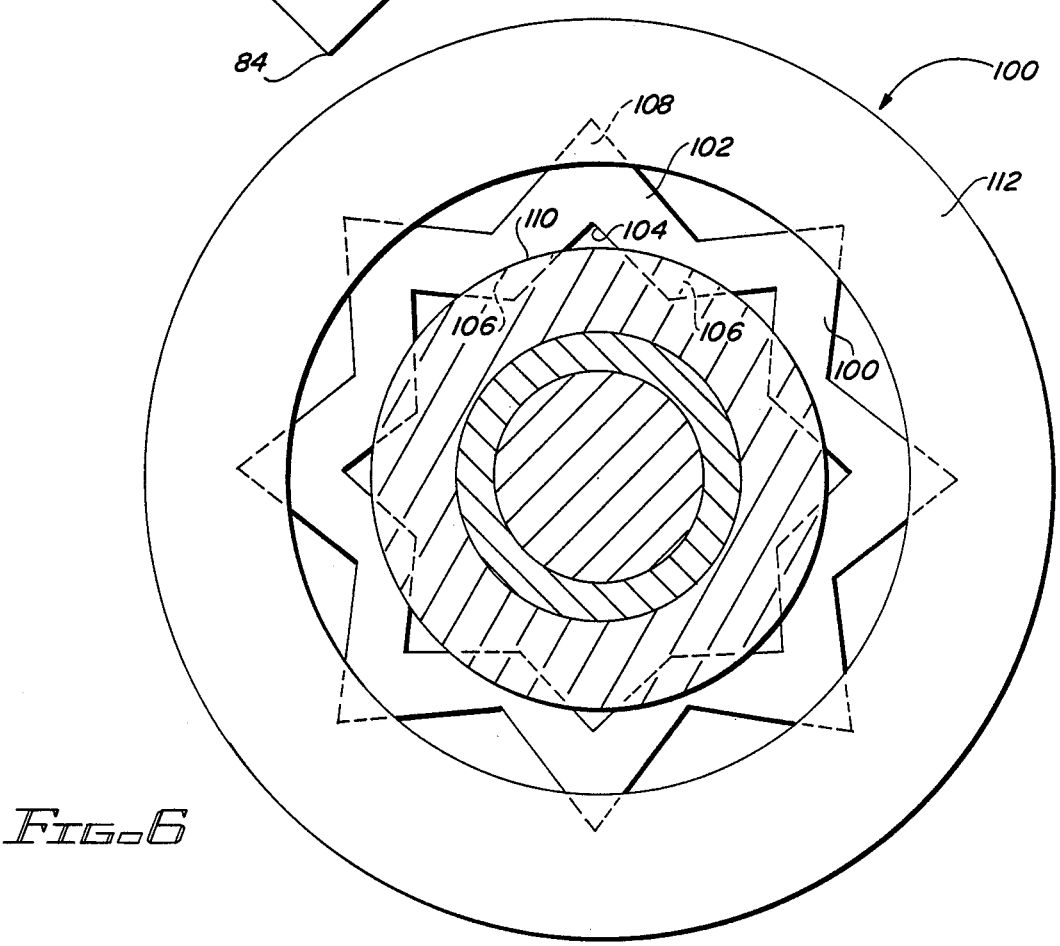
FIG. 6 is a front elevation of another embodiment member 38 in FIG. 3.

In the embodiment of FIG. 6, the disc member 100 includes a plurality of generally triangular-shaped portions 102 which define an inner arch 104, inwardly facing tip ends 106 and outwardly-facing tip ends 108. As is shown, the inwardly-facing tip ends 106 extend into the buffer portion of the sleeve 110, and the outwardly-facing tip ends 108 extend into the sheath 112 that forms the outer periphery of the catheter.

In each of the embodiments shown in FIGS. 3-6, the extremities of the tip ends or inner peripheral surfaces may be beveled so as to obtain an edge contact with both the sleeve and sheath, while ensuring a positive locking in the respective adjacent one of the sleeve or outer sheath. By way of example, the tip end 42 of FIG. 3 is shown in FIG. 7A as including a double bevel to an outer extreme point. The degree of bevel on the surfaces 120 control the depth into which the tip end 42 extends into the sleeve, and thus, the degree of edge contact. Similarly, in FIGS. 7B and 7C, the respective bevel 122 or 124 controls the depths into which the respective tip ends 60 or 84 extend into the sleeve or sheath.

As can be seen from a comparison of FIG. 2 with FIGS. 3-7, the axial connection of each disc member is relatively small with respect to the lateral dimension. Heretofore, the devices used to fix a fiber optic rod at the distal end of a catheter has been relatively elongated in the axial direction with respect to the lateral direction. Consequently, such prior art arrangements are extremely difficult and expensive to place at the distal end of the catheter, requiring threading and similar difficult tasks for very small hardware items. Frequently, the fiber optic rod is fractured, the protective sleeve is damaged, and so forth. The use of the edge contact disc members like that shown in FIGS. 3-7 permit the spacing means at the distal end of the catheter which fixes the fiber optic rod relative to the outer sheath and is very inexpensive relative to prior art devices and may be installed with a much less risk of damage to either the fiber optic rod or its protective sleeve. Further, while such prior art arrangements have required the threading of the spacer means into the outer sheath, the disc members shown in FIGS. 3-7 may be simply engaged with edge contact into the outer sheath via a simple inward crimping of the outer sheath.

It will be understood that various modifications may be employed with connection to the optically transmissive of the present invention without departing from the spirit and scope of the present invention.

What is claimed is:

1. An optical energy transmission device comprising:
   a fiber optic rod having a protective sleeve;
   a sheath surrounding and spaced from said fiber optic rod and sleeve; and
   at least one spacing disc having plural tip ends extending in edge contact with said sleeve and engaging said sheath for supporting said fiber optic rod within said sheath, said spacing disc having a discontinuity for permitting the expansion and contraction of said disc.

2. The optical energy transmission device recited in claim 1 wherein said supporting means comprises a spacing member between said fiber optic rod and said sheath, said spacing member having a lateral dimension normal to said rod and sheath which is greater than its axial dimension parallel with said rod and sheath.

3. The optical energy transmission device recited in claim 1 wherein said disc member further includes at least three inwardly-facing supporting edge portions fixed with said sleeve.

4. The optical energy transmission device recited in claim 3 wherein said inwardly-facing portions comprise said tip ends extending into edge contact with said sleeve to fix each said disc member with said sleeve.

5. The optical energy transmission device recited in claim 4 wherein the periphery of said opening forms an inner arch between adjacent inwardly-facing tip ends, each inner arch forming a void between its inner extremity and its outer periphery of said sleeve where said inner arches form plural passageways through said disc member for cooling fluids to pass along the outer periphery of said fiber optic rod and sleeve.

6. The optical energy transmission device recited in claim 5 further comprising at least four outwardly-facing tip ends along the outer periphery of said disc member, said outwardly-extending tip ends extending into edge contact with the inner periphery of said sheath.

7. The optical energy transmission device recited in claim 6 wherein the periphery of said disc member forms an outer arch between adjacent outwardly-facing tip ends, each outer arch forming a void between its inner extremity and the inner periphery of said sheath, so that cooling fluids pass therethrough.

8. The optical energy transmission device recited in claim 1 further comprising at least three outwardly-facing supporting portions along the outer periphery of said disc member, said outwardly-extending supporting portions extending into edge contact with the inner periphery of said sheath.

9. The optical energy transmission device recited in claim 2 wherein said spacing member comprises means for permitting fluid flow along said spacing member between said fiber optic rod and said sheath.

10. An optical energy transmission device comprising:
    an elongated, flexible fiber optic rod with a generally uniform cross-section along a portion of its length and having a protective sleeve along the outer periphery thereof;
    a flexible sheath having a hollow longitudinal core with said fiber optic rod and sleeve extending axially therethrough and with the inside diameter of said sheath being substantially greater than the outer periphery of said rod-sleeve combination so as to permit a cooling fluid to pass along the space between the inner periphery of said sheath and the outer periphery of said sleeve; and
    plural spacing discs, each having a central opening for receiving said fiber optic rod and sleeve combination and having tip ends extending into both said sleeve and said sheath in edge contact for supporting and spacing said fiber optic rod within said hollow core, said spacing discs having voids for permitting the cooling fluid to pass along said sleeve during passage along said hollow core.

11. The optical energy transmission device recited in claim 10 wherein the periphery of said opening forms an inner arch between adjacent inwardly-facing tip ends, each inner arch forming a void between its inner extremity and the outer periphery of said sleeve, whereby said inner arches form plural passageways for the cooling fluid.

12. The optical energy transmission device recited in claim 1 further comprising at least six outwardly-facing tip ends along the outer periphery of each disc, said outwardly-extending tip ends extending into contact with the inner periphery of said sheath and wherein the outer periphery of each disc forms an outer arch between adjacently outwardly-facing tip ends, each outer arch forming a void between its inner extremity and the inner periphery of said sheath to permit the passage of the cooling fluid.

13. A flexible optically transmissive catheter for percutaneous insertion into a body cavity, comprising:
- an elongated flexible sheath having a hollow core;
- an elongated flexible fiber optic rod having an outer protective sleeve and a generally uniform cross-section across at least a portion of its length, said fiber optic rod-sleeve combination having a diameter which is substantially less than the inner periphery of said sheath so that a cooling fluid may be passed along said hollow core and across the periphery of said fiber optic rod-sleeve combination; and
- plural, independent spacing discs, each having a central opening to receive the rod-sleeve combination and each having tip ends extending into said sleeve and said sheath in edge contact for supporting and spacing said fiber optic rod within said outer core, each said disc having voids for permitting a cooling fluid to pass along said fiber optic rod and through said hollow core.

14. The flexible optically transmission catheter recited in claim 13 wherein each said disc has a lateral dimension normal to said rod and sheath which is greater than its axial dimension parallel with said rod and sheath.

* * * * *